(12) United States Patent
Seo et al.

(10) Patent No.: US 9,956,204 B2
(45) Date of Patent: May 1, 2018

(54) COMPOSITION FOR EXTERMINATING SCUTICOCILIATES IN FISH INCLUDING MEBENDAZOLE

(71) Applicant: NATIONAL INSTITUTE OF FISHERIES SCIENCE, Busan (KR)

(72) Inventors: Jung Soo Seo, Sejong-si (KR); Na Young Kim, Ulsan (KR); Sung-hee Jung, Busan (KR); Myoung Sug Kim, Busan (KR)

(73) Assignee: NATIONAL INSTITUTE OF FISHERIES SCIENCE, Busan (KR)

( * ) Notice: Subject to any disclaimer, the term of this patent is extended or adjusted under 35 U.S.C. 154(b) by 0 days. days.

(21) Appl. No.: 15/620,788

(22) Filed: Jun. 12, 2017

(65) Prior Publication Data

US 2017/0360758 A1    Dec. 21, 2017

(30) Foreign Application Priority Data

Jun. 16, 2016  (KR) .......................... 10-2016-0075006

(51) Int. Cl.
*A61K 31/415* (2006.01)
*A61K 31/4184* (2006.01)
*A61K 9/00* (2006.01)

(52) U.S. Cl.
CPC ........ *A61K 31/4184* (2013.01); *A61K 9/0053* (2013.01)

(58) Field of Classification Search
CPC .......................... A61K 31/4184; A61K 9/0053
See application file for complete search history.

(56) References Cited

FOREIGN PATENT DOCUMENTS

| KR | 10-0379026 B1 | 3/2003 |
|----|---------------|--------|
| KR | 10-0784917 B1 | 12/2007 |
| KR | 10-1434553 B1 | 8/2014 |
| KR | 10-1544049 B1 | 8/2015 |

OTHER PUBLICATIONS

Kang et al, Aquaculture (Year: 2013).*
Schmahl et al, Parasitlology Research (Year: 1998).*
Taraschewski et al, Parasitology Research (Year: 1988).*
Lange, S., et al., "Humoral immune parameters of cultured Atlantic halibut (*Hippoglossus hippoglossus* L.)", "Fish & Shellfish Immunology", Aug. 2001, pp. 523-535, vol. 11.
Barry, R. M., et al., "A Rapid and Sensitive Assay of Muramidase", "Proceedings of Society for Experimental Biology Medicine", Feb. 9, 1965, pp. 384-386, vol. 119.
Seung, L., "Commercialization of first-line treatment for halibut farmers", "The Kookje Daily News", Dec. 31, 2015.

\* cited by examiner

*Primary Examiner* — Kortney L. Klinkel
*Assistant Examiner* — Ibrahim D Bori
(74) *Attorney, Agent, or Firm* — Hultquist, PLLC; Steven J. Hultquist

(57) ABSTRACT

The present disclosure relates to a composition for exterminating scuticociliates in fish, comprising Mebendazole as an active ingredient, and to a method for exterminating scuticociliates by performing oral administration or immersion administration of Mebendazole in fish. According to the present disclosure, the composition and the extermination method have excellent effects in exterminating scuticociliates in fish, and can be efficiently used in the aquaculture industry by performing oral administration or immersion administration.

5 Claims, 1 Drawing Sheet
(1 of 1 Drawing Sheet(s) Filed in Color)

COMPOSITION FOR EXTERMINATING SCUTICOCILIATES IN FISH INCLUDING MEBENDAZOLE

CROSS-REFERENCE TO RELATED APPLICATIONS

This application claims priority under 35 U.S.C. § 119 of Korean Patent Application No. 10-2016-0075006 filed on Jun. 16, 2016. The disclosure of such Korean priority patent application is hereby incorporated herein by reference in its entirety, for all purposes.

BACKGROUND

Field

The present disclosure relates to a composition for exterminating scuticociliates in fish, in which the composition includes Mebendazole, and more particularly to a composition for exterminating scuticociliates in fish, in which the composition includes Mebendazole as an active ingredient, and to a method for exterminating scuticociliates by performing the oral administration or the immersion administration of Mebendazole in fish.

Description of the Related Art

According to the UN report, the world population is projected to increase exponentially from 7 billion to 9.1 billion by 2050, and food demand is expected to increase by more than 70%. With this increase in population, the interest in global food security has increased rapidly. Recently, the awareness of food supply safety and food safety has risen sharply with the increase of income and improvement of educational standards.

In response to this trend, Korea's aquaculture industry has been rapidly developed. The proportion of aquaculture industry in total fishery output has increased by 137% from 653,000 tons in 2000 to 1,547,000 tons in 2014. Among them, the aquaculture output of seawater fish is continuously increasing. The major seawater cultured fishing species in Korea are olive flounder, black rockfish, mullet, red seabream, and sea bass. When fish are cultured, unlike the natural state, they are cultured in a closed environment. Hence, depending on the aquaculture environment, various diseases are caused. In particular, due to water pollution, old facility of aquaculture system, recessiveness of a species of fish, overcrowding, and the like, various diseases have been caused. The mortality amount of cultured fishes caused thereby is very high, resulting in severe loss of aquaculture fishery household income. Scuticociliatosis is a typical disease that infects and damages cultured fish.

Scuticociliatosis is a parasitic disease caused by scuticociliates belonging to scuticociliatida that invades and are parasitic on the internal organs (brain, kidney, spleen, spinal cord) as well as the external organs (body surface, gills). Scuticociliates have scutica (a ring or whip-shaped organ that is temporarily shown) that is a unique system on the inside and are easily distinguished from the other ciliates. However, the scuticociliates that are parasitic on a fish body are not visible to the naked eyes, but are visible with a microscope (100 Magnifications). Scuticociliates are in the shape of a fusiform or cucumber seed and have cilia in the whole body of the worm. They actively exercise and dig through fish cells with the front end (somewhat sharp) and gnaw host cells with the mouth in the center of the worm.

When they are infected with scuticociliates, ulceration is shown such that the epidermis of the infected fish is peeled off and the muscle layer is exposed. Symptoms such as body surface inflammation, fin soft ray, caudal peduncle exposure, head injury (snout bleeding, ocular opacity and protrusion, oral mucosal congestion) are shown. When the infected fish are dissected, liquefied necrosis of the brain tissue, melting and necrosis symptoms of connective tissues are shown according to the infection site, and in a field of seeding that produces seeds, it is prevalent that the head and body surface turn white and juvenile fish die in large quantities.

In the early 1990s, scuticociliatosis was characterized mainly by the formation of ulcers on the body surface of juvenile fish in a seed production field in spring, when the breeding water temperature was maintained at 14 to 17° C. From the mid-1990s, however, not only the onset water temperature was spread to 10 to 17° C. from winter to spring, but also the tendency was marked such that the outbreak of scuticociliatosis becomes even wider from juvenile fish to 1-year-old fish (10 to 25 cm). Meanwhile, from the latter half of 1990, there is a tendency that it occurs throughout the year, regardless of water temperature, and the phenomenon is prominent that infectious fishing species are expanded.

In the 2000s, scuticociliatosis still occurs throughout the year, regardless of water temperature, infecting all fish of olive flounder, and have a wide variety of external symptoms. In the adult olive flounder, infectious symptoms are characterized by the congestion in the snout area with circling, or circling and insanity with no symptom. In this case, there are many cases that most of fish is infected with a large amount of scuticociliates in the brain. Externally, it is necessary to suspect that it is caused by scuticociliates once the body surface of the cultured fish is rough or the ulcer is formed, and corrosion of the snout and tail is observed, or it is seen that the head and gill lid are turning red. In addition, when body surface mucus, gill mucus or brain tissue are separated, put on a slide and looked at the microscope (100 Magnifications), if a worm seems to gnaw cells while swinging cilia, it can be determined to be diagnosed as scuticociliates. Scuticociliates causes a disease, regardless of the size of fish and water temperature. If it infects the body surface, it can be relieved by formalin, but it is impossible to treat it when it is parasitic on the internal organs including the brain and causes systemic infection.

Scuticociliates do not cause a disease to fish inhabiting in nature or in the natural state, but most of them infect fish in aquaculture environment and cause damage. As reported in various European countries, there are sporadic damage to aquarium ornamental fish and massive deaths of tunas cultured in an inclosing net by *Uronema marinum* (*Uronema nigricans*), massive deaths of sea bass cultured in a landbased aquaculture system by *Philasterides dicentrarchi*, and massive deaths of turbots cultured in an aquarium basin by unidentified scuticociliates. Infected fish species include turbot, sea bass, olive flounder, and sevenband grouper. They are resistant to turbots, sea bass, olive flounders, and sevenband groupers. There are reports of pathogenic *Anophyroides haemophila* and the other *U. nigricans, Mesanophrys carcini, Orchitophyra stellarum, Tetrahymena corlissi*, and pathogenic *M. avidus* (=*P. dicentrarchi*) in turbots, sea bass, and olive flounders. Since the 1990s, scuticociliatosis occurs in turbots in the Atlantic coast, sea bass farms in the Mediterranean coast, and in East Asia and Europe, and have caused serious economic loss. In Japan, the occurrence was high in the ground olive flounder farms using underground seawater with low salt concentration.

Currently, techniques for exterminating scuticociliatosis by direct administration to olive flounder include the oral administration anthelmintic of ketoconazole (Korean Patent Registration No. 10-0379026), immersion (immersion administration) anthelmintic using butylaldehyde (Korean Patent Registration No. 10-0784917), and immersion anthelmintic comprising quaternary ammonium salts and bronopol as active ingredients (Korean Patent Registration No. 10-1544049). However, in 2011, the French Health Products Safety Agency (AFSSAPS) decided to discontinue sales and retrieve the same preparation due to the serious hepatotoxicity induction of ketoconazole (antifungal agent) oral preparation. At that time, the Korea Food and Drug Administration also announced action plans for a comprehensive review of the overall safety, and many problems were reported in 2013, such as discontinuing sales of oral products of the same preparation and deciding on a second grade recovery measure.

Meanwhile, in Korea, after the malachite green matter in 2005, it became necessary to use formalin under the system after obtaining approval as an aquaculture drug, which had been commercially used and recognized to have an efficacy effect in the past in the treatment of scuticociliatosis in cultured olive flounder. The National Institute of Fisheries Science has developed fish formalin as anthelmintic and has supported to obtain an item approval from the (formerly) National Veterinary Research and Quarantine Service, and this product has been used as the only anthelmintic for scuticociliates thus far. However, since formalin has been used in olive flounder farms for a long time since the 1990s, there has been a problem of decreasing the efficacy of formalin as anthelmintic in the field. In reality, it was confirmed that water temperature (temperature), turbidity, and high density have particularly the most direct impact on the efficacy of formalin depending on the aquaculture environment such as Pohang, Wando, Jeju areas. Meanwhile, an anthelmintic drug (Korean Patent Registration No. 10-1434553) comprising hydrogen peroxide as an active ingredient received an item approval as a olive flounder scuticociliates anthelmintic for the first time in 2015. However, these scuticociliates anthelmintic of immersion administration is effective in exterminating scuticociliates infected externally such as gills or body surfaces, but it is impossible to exterminate scuticociliates infected in the internal organs. Thus, the development of anthelmintic for oral administration is urgently required.

Under these technical backgrounds, as a result that the present inventors did their best to develop safety-guaranteed anthelmintic capable of exterminating scuticociliates, they confirmed that Mebendazole is effective in exterminating scuticociliates, and completed the present disclosure.

PRIOR ART DOCUMENTS

Patent Documents (Patent Document 1) Korean Registered Patent No. 10-0379026
(Patent Document 2) Korean Registered Patent No. 10-1434553

SUMMARY

It is an object of the present disclosure to provide a novel composition and feed for exterminating scuticociliates in fish.

It is another object of the present disclosure to provide a novel method for exterminating or preventing scuticociliates in fish.

In order to achieve the above object, the present disclosure provides a composition for exterminating scuticociliates in fish, in which the composition comprises Mebendazole as an active ingredient.

The present disclosure also provides a feed for fish, in which the feed comprises Mebendazole.

The present disclosure also provides a method for exterminating scuticociliates in fish, in which the method comprises administering the composition to fish.

The present disclosure also provides a method for preventing scuticociliatosis, in which the method comprises adding Mebendazole to kill scuticociliates in breeding water.

The composition and the exterminating method according to the present disclosure are very excellent in terms of effect of exterminating scuticociliates in fish, and are safe with no side effects on fish. Not only immersion administration but also oral administration is possible. Thus, they may be usefully utilized in the aquaculture industry.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENT

Figure 1:
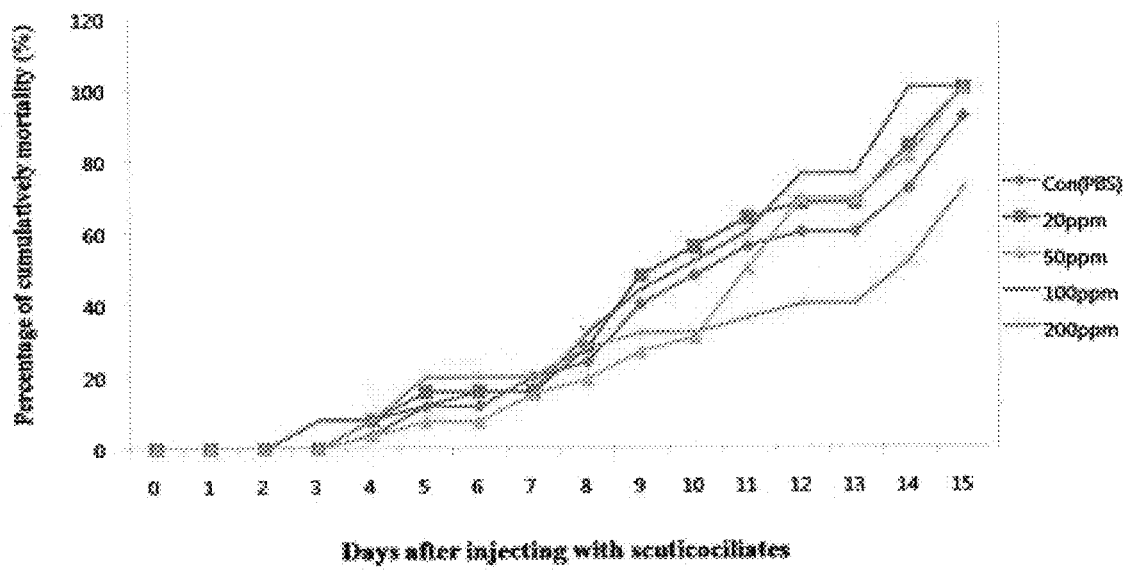
FIG. 1 illustrates the clinical test results of a cumulative mortality rate according to the concentration of immersion administration of Mebendazole.

Unless otherwise defined, all technical and scientific terms used in the present specification have the same meanings as commonly understood by a skilled expert in the technical field to which the present disclosure belongs. Generally, the nomenclature used in the present specification described hereinafter is well known and is commonly used in the present technical field.

In order to develop anthelmintic capable of exterminating scuticociliates in fish, the present inventors searched the entire DB of the drug anthelmintic which received an item approval for livestock and conducted a search on the various documents. As a result, a total of 19 candidate substances could be selected as shown in Table 1 below. As a result of measuring the killing effect of scuticociliates by concentration for 19 candidate substances, it was confirmed that Mebendazole shows an effective killing effect of scuticociliates at a very low concentration.

TABLE 1

| No | Active Ingredient | Effect | Permission for Fishery use in Korea |
|---|---|---|---|
| 1 | Albendazole | Extermination of eelworm, lungworm., tapeworm, *Fasciola hepatica* in livestock | x |
| 2 | Febantel | Extermination of lungworm, tapeworm, whipworm, etc. in livestock | x |

TABLE 1-continued

| No | Active Ingredient | Effect | Permission for Fishery use in Korea |
|---|---|---|---|
| 3 | Fenbendazole | Extermination of eelworm, lungworm, giantkidney worm in livestock | x |
| 4 | Mebendazole | Extermination of roundworm, tapeworm, stomach worm, lungworm, etc. in livestock | x |
| 5 | Oxfendazole | Extermination intestinal parasite imago, larva in livestock | x |
| 6 | Levamisol | Extermination of lungworm, roundworm, eelworm in livestock | x |
| 7 | Piperazine | Extermination of roundworm, pin worm, filarial worm, common nodular worm | x |
| 8 | Pyrantel | Extermination of roundworm, ancylostomiasis, pin worm in livestock | x |
| 9 | Tetramisole | Extermination of lungworm, roundworm, common nodular worm, lungworm in livestock | x |
| 10 | Oxibendazole | Extermination of roundworm, eelworm in livestock | x |
| 11 | Ivermectin | Extermination of eelworm, lungworm, external parasite in livestock | x |
| 12 | Abamectin | — | x |
| 13 | Moxidectin | Extermination of heart worm in dog (for pets) | x |
| 14 | Selamectin | Treatment of dermatitis, Extermination of roundworm in dog and cat(for pet) | x |
| 15 | Imidacloprid | Insecticide | x |
| 16 | Trichlorfon | Treatment of parasitic disease in carp or eel | o |
| 17 | Benzyl benzonate | Medicine for skin disease | x |
| 18 | Clorsulon | External or internal anthelmintic for livestock | x |
| 19 | Deltamethrin | Insecticide | x |

Accordingly, in one aspect, the present disclosure provides a composition for exterminating scuticociliates in fish comprising Mebendazole as an active ingredient.

Mebendazole is a synthetic benzimidazole and is mostly an organic solvent and yellow in color, and is a compound having a molecular weight of 295. Only a portion of the oral dose is absorbed and within 24~48 hours, 10% is excreted in the urine, and most of the products excreted by kidneys are decarboxylated metabolites. Mebendazole inhibits the glucose uptake of a worm to induce glycogen deficiency, causing the worm to die, and with regard to some parasites, the effects thereof are known for human and livestock uses. Mebendazole is known to have no side effects, but may cause temporary gastrointestinal symptoms and headache when used in the human body. Currently, it is known that it is used for ascariasis, taeniasis, enterobiasis, etc. However, it is known that the effect on trichuriasis is weak and it has no effect on anisakiasis.

In the present disclosure, the term "active ingredient" refers to a substance or substance group which is expected to directly or indirectly express the efficacy or effect of the drug by an inherent pharmacological action, and means comprising a main ingredient.

In one embodiment, the composition for exterminating scuticociliates in fish containing Mebendazole as an active ingredient of the present disclosure may be a pharmaceutical preparation, and the pharmaceutical preparation of the present disclosure may be administered together with a pharmaceutically acceptable carrier. At the time of oral administration, in addition to the active ingredient, a binder, a lubricant, a disintegrant, an excipient, a solubilizing agent, a dispersing agent, a stabilizer, a suspending agent, a colorant, a perfume, and the like may be further included. In the case of injections, the pharmaceutical preparations of the present disclosure may be used by mixing them with buffering agents, preservatives, analgesics, solubilizers, isotonic agents, stabilizers, and the like. In addition, at the time of topical administration, the pharmaceutical preparation of the present disclosure may use a base, an excipient, a lubricant, a preservative, and the like.

As described above, the formulation of the pharmaceutical preparations of the present disclosure may be variously prepared by mixing it with a pharmaceutically acceptable carrier, and in particular, it may be prepared as a formulation for oral administration or immersion administration.

In another aspect, the present disclosure relates to a feed additive composition. The ingredients contained in the feed additive composition of the present disclosure include ingredients commonly used in feed additive compositions in addition to Mebendazole as an active ingredient, and may include various known functional materials for feed additives such as growth promoting substances and substances for reinforcing immunity, etc.

The feed additive composition of the present disclosure may be prepared into any formulation that is commonly prepared in the pertinent art, and it may be formulated into, for example, solutions, suspensions, emulsions, oils or powders, etc. but is not limited thereto.

In another aspect, the present disclosure relates to a method for exterminating scuticociliates in fish, comprising administering a composition for exterminating scuticociliates to fish, in which the composition includes Mebendazole as an active ingredient to fish.

In the present disclosure, the administration is preferably oral administration or immersion administration, but is not limited thereto.

In other words, the composition of the present disclosure may be administered orally or parenterally, and the route of administration according to the present disclosure is not limited thereto. For example, oral, intramuscular, intraperitoneal, topical administration, and immersion administration are possible. For such clinical administration, the composition of the present disclosure may be prepared as a suitable formulation using known techniques.

In the present disclosure, the preferred administration concentration of Mebendazole is 10 to 500 ppm, more preferably 150 to 300 ppm for oral administration, 10 to 300 ppm for immersion administration, and most preferably 200 ppm for oral administration, and 30 to 100 ppm for immersion administration, but is not limited thereto.

In the present disclosure, the immersion administration may comprise a single immersion administration of Mebendazole for 2 to 4 hours at a concentration of 50 to 300 ppm or multiple administrations for 3 to 10 days at a concentration of 10 to 50 ppm which includes replacing drugs every day, but is not limited thereto.

In the present disclosure, the effective dose varies in range depending on the size, mass, administration time, administration method, health condition, severity of disease, etc. of the fish to be treated, and may be determined by an ordinary skilled person in the pertinent technical field.

The composition and method of the present disclosure may be used alone or in combination with other drug treatments and methods using a biological response modifier for exterminating scuticociliates.

Meanwhile, since the inventors of the present disclosure could confirm that Mebendazole kills scuticociliates in vitro at a low concentration for a short period of time, the present inventors found that it is possible to destroy scuticociliates existing in the seawater collected as breeding water to prevent the occurrence of scuticociliatosis in the water tank, and to prevent the spread of infection to healthy fish from the fish which are infected by scuticociliates in the water layer.

Accordingly, in one aspect, the present disclosure provides a method for preventing scuticociliatosis comprising adding Mebendazole to kill scuticociliates in breeding water.

The fish that is the subject of the composition for exterminating scuticociliates, feed, extermination method, or prevention method of the present disclosure is not limited by its type as long as it is fish on which scuticociliatosis occurs, but in particular, it may be fish such as olive flounder, black rockfish, red seabream and sea bass, etc.

Hereinafter, the present disclosure will be described in more detail by way of examples. It will be apparent to a person having ordinary skill in the pertinent art that these examples are for illustrative purposes only and that the technical scope of the present disclosure is not construed as being limited by these examples.

Example 1: Selection of Candidate Substances for Scuticociliates Extermination Drugs The candidate substances for scuticociliates extermination drugs were selected after a search on the animal medicine homepage DB of the (formerly) Agriculture, Forestry and Fishery Quarantine Inspection Agency and various domestic and foreign documents. The candidate substances were selected on the basis of animal (livestock) medicines which received an item approval so as to enable rapid industrialization after confirmation of efficacy. Finally, a total of 19 candidate substances were selected: Albendazole, Febantel, Fenbendazole, Mebendazole, Oxfendazole, Levamisol, Piperazine, Pyrantel, Tetramisole, Oxibendazole, Ivermectin, Abamectin, Moxidectin, Selamectin, Imidacloprid, Trichlorfon, Benzyl benzonate, Clorsulon, and Deltamethrin. An attempt was tried to confirm whether these candidate substances have an effect for exterminating scuticociliates.

Example 2: Comparison of Scuticociliates Extermination Effect of Candidate Substances in an Mem Medium CHSE-214 cell line into which scuticociliates were inoculated was cultured in advance. The CHSE-214 cell line was cultured in an incubator using an MEM medium at 22° C. Scuticociliates inoculated into the cell line proliferated for 3 days by which the number reaches to be capable of analyzing in vitro anti-scuticociliates effect. Scuticociliates that feed on the cell line and sufficiently grow were mixed with the candidate substance and the activity of scuticociliates was measured.

In order to analyze the antiparasitic activity of the above 19 types of candidate substances of scuticociliates extermination drugs, scuticociliates were cultured for 3 days, and 100 µl ($1\times10^5$) was dispensed into each well of 96 wells. The candidate substances were diluted by each concentration and the final volume was dispensed into 100 µl. Thereafter, the two were mixed and finally made into 200 µl. They were cultured by time and the activity and shape of scuticociliates were observed with a microscope. The same experiment was repeated 3 times, and the result shows that Mebendazole has the effect of killing scuticociliates at the lowest concentration (Table 2).

TABLE 2

| No | Active Ingredient | Dosage(ppm) | | | | | | | | | | | |
|----|------|---|---|---|---|---|---|---|---|---|---|---|---|
| 1 | Albendazole | 10 Survival | 50 Survival | 100 Survival | 200 Survival | 300 Survival | 400 Survival | 500 Survival | 600 Survival | 700 Survival | 800 Δ | 900 Death | 1000 Death |
| 2 | Febantel | 10 Survival | 50 Survival | 100 Survival | 200 Survival | 300 Survival | 400 Survival | 500 Survival | 600 Survival | 700 Survival | 800 Survival | 900 Survival | 1000 Survival |
| 3 | Fenbendazole | 10 Survival | 50 Survival | 100 Survival | 200 Survival | 300 Survival | 400 Survival | 500 Survival | 600 Survival | 700 Survival | 800 Δ | 900 Δ | 1000 Death |
| 4 | Mebendazole | 10 Survival | 50 Survival | 100 Death | 200 Death | 300 Death | 400 Death | 500 Death | 600 Death | 700 Death | 800 Death | 900 Death | 1000 Death |
| 5 | Oxfendazole | 10 Survival | 50 Survival | 100 Survival | 200 Survival | 300 Survival | 400 Survival | 500 Survival | 600 Survival | 700 Δ | 800 Δ | 900 Δ | 1000 Death |
| 6 | Levamisol | 500 Survival | 1000 Survival | 1500 Survival | 2000 Survival | 2500 Survival | 3000 Survival | 3500 Survival | 4000 Survival | — | — | — | — |
| 7 | Piperazine | 500 Survival | 1000 Survival | 1500 Survival | 2000 Survival | 2500 Survival | 3000 Survival | 3500 Survival | 4000 Survival | — | — | — | — |
| 8 | Pyrantel | 500 Survival | 1000 Survival | 1500 Survival | 2000 Survival | 2500 Survival | 3000 Survival | 3500 Survival | 4000 Survival | — | — | — | — |
| 9 | Tetramisole | 500 Survival | 1000 Survival | 1500 Survival | 2000 Survival | 2500 Survival | 3000 Survival | 3500 Survival | 4000 Survival | — | — | — | — |
| 10 | Oxibendazole | 500 Survival | 1000 Survival | 1500 Δ | 2000 Δ | 2500 Death | 3000 Death | 3500 Death | 4000 Death | — | — | — | — |
| 11 | Ivermectin | 500 Survival | 1000 Survival | 1500 Survival | 2000 Survival | 2500 Survival | 3000 Survival | 3500 Survival | 4000 Survival | — | — | — | — |
| 12 | Abamectin | 10 Survival | 20 Survival | 50 Survival | 100 Survival | 150 Survival | 200 Δ | 400 Death | 500 Death | — | — | — | — |
| 13 | Moxidectin | 100 Survival | 200 Survival | 400 Survival | 500 Δ | 800 Death | 1000 Death | 2000 Death | 3000 Death | — | — | — | — |
| 14 | Selamectin | 10 Survival | 20 Survival | 50 Survival | 100 Survival | 200 Survival | 250 Survival | 500 Δ | 1000 Death | — | — | — | — |
| 15 | Imidacloprid | 500 Survival | 600 Survival | 700 Survival | 800 Survival | 900 Δ | 1000 Δ | 2000 Death | 5000 Death | — | — | — | — |
| 16 | Trichlorfon | 200 Survival | 500 Survival | 600 Δ | 700 Death | 800 Death | 900 Death | 1000 Death | — | — | — | — | — |

TABLE 2-continued

| No | Active Ingredient | Dosage(ppm) | | | | | | | | | | | |
|---|---|---|---|---|---|---|---|---|---|---|---|---|---|
| 17 | Benzyl benzonate | 10 | 50 | 100 | 200 | 500 | 600 | 800 | 1000 | — | — | — | — |
| | | Survival | Survival | Survival | Survival | Survival | Survival | Δ | Δ | — | — | — | — |
| 18 | Clorsulon | 500 | 700 | 800 | 900 | 1000 | 2000 | 4000 | — | — | — | — | — |
| | | Survival | Survival | Survival | Δ | Δ | Death | Death | — | — | — | — | — |
| 19 | Deltamethrin | 500 | 600 | 700 | 800 | 900 | 1000 | 2000 | 5000 | — | — | — | — |
| | | Survival | Survival | Survival | Survival | Survival | Δ | Death | Death | — | — | — | — |

Example 3: Comparison of Scuticociliates Extermination Effect of Candidate Substances in Seawater Medium Conditions Since scuticociliates anthelmintic intends to inhibit the infection of scuticociliates of the cultured fish, an attempt was tried to confirm whether the above 19 types of candidate substances of scuticociliates extermination drugs exhibit the same effect as that of the Example 2 also under the seawater conditions not under MEM medium. For this, scuticociliates were cultured in CHSE-214 cell line (using MEM medium), and then scuticociliates were collected and centrifuged with sterilized seawater or artificial seawater (20‰) to replace them with a seawater medium. Each of 100 μl ($1\times10^5$) was dispensed into each well of 96 wells, followed by further culture for 30 minutes. The candidate substances diluted in seawater to have a volume of 100 μl per each concentration were mixed with scuticociliates to have the final volume of 200 μl and cultured for 4 hour. The activity and shape of scuticociliates were observed with a microscope. The same experiment was repeated 3 times, and the result shows that Mebendazole most effectively kills scuticociliates as in an MEM medium (Table 3).

TABLE 3

| No | Active Ingredient | Dosage(ppm) | | | | | | | | | | | |
|---|---|---|---|---|---|---|---|---|---|---|---|---|---|
| 1 | Albendazole | 10 | 50 | 100 | 200 | 300 | 400 | 500 | 600 | 700 | 800 | 900 | 1000 |
| | | Survival | Survival | Survival | Survival | Survival | Survival | Survival | Survival | Survival | Δ | Death | Death |
| 2 | Febantel | 10 | 50 | 100 | 200 | 300 | 400 | 500 | 600 | 700 | 800 | 900 | 1000 |
| | | Survival | Survival | Survival | Survival | Survival | Survival | Survival | Survival | Survival | Survival | Survival | Survival |
| 3 | Fenbendazole | 10 | 50 | 100 | 200 | 300 | 400 | 500 | 600 | 700 | 800 | 900 | 1000 |
| | | Survival | Survival | Survival | Survival | Survival | Survival | Survival | Survival | Survival | Δ | Δ | Death |
| 4 | Mebendazole | 10 | 50 | 100 | 200 | 300 | 400 | 500 | 600 | 700 | 800 | 900 | 1000 |
| | | Survival | Survival | Death | Death | Death | Death | Death | Death | Death | Death | Death | Death |
| 5 | Oxfendazole | 10 | 50 | 100 | 200 | 300 | 400 | 500 | 600 | 700 | 800 | 900 | 1000 |
| | | Survival | Survival | Survival | Survival | Survival | Survival | Survival | Survival | Δ | Δ | Δ | Death |
| 6 | Levamisol | 500 | 1000 | 1500 | 2000 | 2500 | 3000 | 3500 | 4000 | — | — | — | — |
| | | Survival | Survival | Survival | Survival | Survival | Survival | Survival | Survival | — | — | — | — |
| 7 | Piperazine | 500 | 1000 | 1500 | 2000 | 2500 | 3000 | 3500 | 4000 | — | — | — | — |
| | | Survival | Survival | Survival | Survival | Survival | Survival | Survival | Survival | — | — | — | — |
| 8 | Pyrantel | 500 | 1000 | 1500 | 2000 | 2500 | 3000 | 3500 | 4000 | — | — | — | — |
| | | Survival | Survival | Survival | Survival | Survival | Survival | Survival | Survival | — | — | — | — |
| 9 | Tetramisole | 500 | 1000 | 1500 | 2000 | 2500 | 3000 | 3500 | 4000 | — | — | — | — |
| | | Survival | Survival | Survival | Survival | Survival | Survival | Survival | Survival | — | — | — | — |
| 10 | Oxibendazole | 500 | 1000 | 1500 | 2000 | 2500 | 3000 | 3500 | 4000 | — | — | — | — |
| | | Survival | Survival | Δ | Δ | Δ | Δ | Death | Death | — | — | — | — |
| 11 | Ivermectin | 500 | 1000 | 1500 | 2000 | 2500 | 3000 | 3500 | 4000 | — | — | — | — |
| | | Survival | Survival | Survival | Survival | Survival | Survival | Survival | Survival | — | — | — | — |
| 12 | Abamectin | 500 | 800 | 900 | 1000 | 1500 | 2000 | — | — | — | — | — | — |
| | | Survival | Death | Death | Death | Death | Death | — | — | — | — | — | — |
| 13 | Moxidectin | 300 | 400 | 500 | 600 | 700 | 1000 | — | — | — | — | — | — |
| | | Survival | Survival | Survival | Survival | Survival | Death | — | — | — | — | — | — |
| 14 | Selamectin | 10 | 50 | 100 | 150 | 200 | 250 | 500 | — | — | — | — | — |
| | | Survival | Survival | Survival | Survival | Survival | Δ | Death | — | — | — | — | — |
| 15 | Imidacloprid | 500 | 1000 | 1200 | 1400 | 1500 | 2000 | 2500 | — | — | — | — | — |
| | | Survival | Δ | Δ | Death | Death | Death | Death | — | — | — | — | — |
| 16 | Trichlorfon | 10 | 50 | 100 | 200 | 500 | 600 | 700 | — | — | — | — | — |
| | | Survival | Survival | Survival | Survival | Survival | Death | Death | — | — | — | — | — |
| 17 | Benzyl benzonate | 50 | 100 | 500 | 600 | 700 | 800 | — | — | — | — | — | — |
| | | Survival | Survival | Δ | Death | Death | Death | — | — | — | — | — | — |
| 18 | Clorsulon | 50 | 250 | 500 | 1000 | 1200 | 1400 | 1500 | — | — | — | — | — |
| | | Survival | Survival | Survival | Survival | Survival | Survival | Death | — | — | — | — | — |
| 19 | Deltamethrin | 250 | 500 | 1000 | 1200 | 1400 | 1500 | — | — | — | — | — | — |
| | | Survival | Survival | Survival | Death | Death | Death | — | — | — | — | — | — |

Example 4: Clinical Trial for Exterminating Scuticociliates of Mebendazole

In order to confirm the scuticociliates extermination effect of Mebendazole, olive flounder were artificially infected with scuticociliates. For the artificial infection, $1\times10^5$ of scuticociliates per fish were intraperitoneally injected into a total of 200 juvenile olive flounder (average 10 cm). The experiment was performed by dividing them into 5 groups of every 20 fish per each experiment.

60 minutes. One unit of lysozyme activity was converted into the amount of a sample that decreases the absorbance 0.001/min.

TABLE 4

| Period | Group | | Length (Cm) | Ht (%) | Hb (g/dl) | MCHC (%) | GOT (U/l) | GPT (U/l) | GLU (mg/dl) | ALP (U/l) | TP (g/dl) | TCHO (mg/dl) |
|---|---|---|---|---|---|---|---|---|---|---|---|---|
| 0 | — | | 22 | 30 | 8.5 | 28.8 | 20 | 1.6 | 8.0 | 200 | 3.7 | 212 |
| 6 h | Immersion | 100 | 22 | 26 | 8.4 | 32.3 | 15 | 1.0 | 4.5 | 268 | 4.1 | 220 |
| | | 500 | 21 | 23 | 6.6 | 28.1 | 28 | 2.5 | 12.0 | 175 | 3.8 | 167 |
| | Oral | 100 | 20 | 27 | 8.0 | 30.1 | 29 | 1.7 | 12.3 | 225 | 4.0 | 149 |
| | | 500 | 21 | 35 | 8.9 | 25.6 | 48 | 5.0 | 12.0 | 318 | 5.6 | 245 |
| 24 h | Immersion | 100 | 22 | 30 | 8.3 | 28.0 | 22 | 2.3 | 13.3 | 255 | 3.3 | 270 |
| | | 500 | 20 | 27 | 8.1 | 30.0 | 34 | 3.7 | 11.3 | 262 | 4.2 | 185 |
| | Oral | 100 | 21 | 29 | 8.5 | 29.0 | 29 | 4.7 | 27.0 | 217 | 4.1 | 145 |
| | | 500 | 23 | 37 | 8.5 | 23.2 | 40 | 7.0 | 54.0 | 200 | 5.3 | 224 |
| 2 D | Immersion | 100 | 21 | 25 | 7.3 | 29.6 | 17 | 1.3 | 4.3 | 176 | 4.1 | 207 |
| | | 500 | 22 | 37 | 10.1* | 29.8 | 66 | 5.0 | 8.3 | 195 | 3.5 | 214 |
| | Oral | 100 | 21 | 30 | 7.7 | 25.5 | 38 | 11.3 | 14.3 | 218 | 4.4 | 223 |
| | | 500 | 22 | 35 | 8.9 | 25.5 | 57 | 31.0 | 44.0 | 148 | 5.6 | 193 |
| 7 D | Immersion | 100 | 20 | 27 | 8.1 | 30.1 | 22 | 8.0 | 12.0 | 235 | 3.9 | 233 |
| | | 500 | 22 | 32 | 9.1 | 28.3 | 27 | 10.3 | 14.7 | 209 | 4.1 | 224 |
| | Oral | 100 | 22 | 35 | 8.9 | 25.1 | 43 | 19.7 | 33.3 | 178 | 4.5 | 267 |
| | | 500 | 22 | 38 | 9.3 | 24.6 | 52 | 16.3 | 27.7 | 205 | 4.7 | 282 |
| 14 D | Immersion | 100 | 23 | 30 | 8.9 | 30.0 | 18 | 8.0 | 14.7 | 221 | 3.2 | 297 |
| | | 500 | 22 | 29 | 10.2* | 35.5 | 34 | 12.7 | 14.3 | 234 | 4.0 | 271 |
| | Oral | 100 | 23 | 27 | 8.4 | 30.1 | 20 | 5.7 | 19.0 | 258 | 4.0 | 230 |
| | | 500 | 24 | 32 | 9.8 | 31.1 | 35 | 20.7 | 41.0 | 288 | 3.4 | 265 |

*$p < 0.05$

In the oral administration experiment, the feed in which each of 20, 50, 100 and 200 ppm of Mebendazole was moisture-absorbed were orally administered once, and the cumulative mortality rate was observed for 15 days. As a result, it was confirmed that the cumulative mortality rate was remarkably decreased at the concentration of 200 ppm (FIG. 1).

Figure 2:
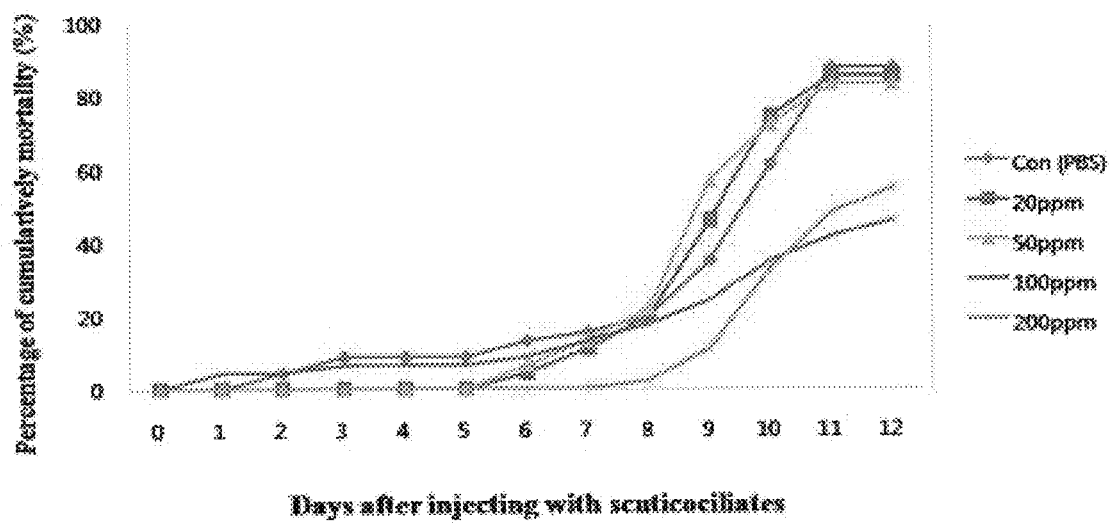
FIG. 2 illustrates the clinical test results of a cumulative mortality rate according to the concentration of oral administration of Mebendazole.

Meanwhile, in the immersion administration experiment, the immersion administration was performed with Mebendazole of each of 20, 50, 100, and 200 ppm for 1 hour, and the cumulative mortality rate was observed for 15 days. As a result, it was confirmed that the cumulative mortality rate was remarkably decreased at the concentration of 100 ppm (FIG. 2).

Example 5: Safety Test According to Administration Clinical Trial of Mebendazole Mebendazole was orally or immersing administered at a concentration of 100 or 500 mg/kg BW (ppm) to the olive flounder once for 1 hour. After 6 hours, 1 day, 2 days, 7 days and 14 days, a blood chemistry analysis and an immunological analysis were conducted.

The blood chemistry analysis was conducted using Fuji-Dri Chem 4500 (Fuji company, Japan) to measure hemoglobin (Hb), hematocrit (Ht), glucose (GLU), total protein (TP), total cholesterol (TCHO), GOT/GPT and lactic acid (LDH), etc.

The immunological analysis was conducted to measure the lysozyme activity of the kidney, spleen and serum (Lange et al., 2001, Parry, R. M. Chandau, R. C. & Shahani, R. M. (1965). A rapid and sensitive assay of muramidase. Proceedings of the Society for Experimental Biology Medicine 119, 384-386). In brief explanation, 100 μl of the prepared plasma was diluted with PBS (pH 6.2) in 2-fold to 4 steps on a 96-well plate and 100 μg of *Micrococcus lysodekiticus* (Sigma, USA) liquid diluted with PBS (pH 6.2) to 0.4 mg/ml was added to each well. After that, absorbance at 590 nm was measured every 0, 15, 30, 45 and

TABLE 5

| | | | Lysozyme activity | | |
|---|---|---|---|---|---|
| Period | Group | | Serum (U/ml) | Kidney (U/ml) | Spleen (U/mg) |
| 0 | — | | 631 | 652 | 665 |
| 6 h | Immersion | 100 | 545 | 644 | 557 |
| | | 500 | 502 | 748 | 513 |
| | Oral | 100 | 573 | 565 | 770 |
| | | 500 | 734 | 680 | 854 |
| 24 h | Immersion | 100 | 557 | 800 | 693 |
| | | 500 | 661 | 893 | 854 |
| | Oral | 100 | 410 | 785 | 823 |
| | | 500 | 436 | 895 | 613 |
| 2 D | Immersion | 100 | 663 | 790 | 714 |
| | | 500 | 526 | 978 | 801 |
| | Oral | 100 | 532 | 852 | 831 |
| | | 500 | 532 | 700 | 692 |
| 7 D | Immersion | 100 | 657 | 816 | 828 |
| | | 500 | 656 | 773 | 789 |
| | Oral | 100 | 452 | 749 | 809 |
| | | 500 | 591 | 789 | 709 |
| 14 D | Immersion | 100 | 910 | 871 | 796 |
| | | 500 | 882 | 980 | 874 |
| | Oral | 100 | 930 | 651 | 773 |
| | | 500 | 960 | 903 | 652 |

In the case of immersion administration of Mebendazole with a single concentration, when the drug concentration increases, the concentration of Hb in the blood slightly increases, but the MCHC numerical values did not show any significant differences (Table 4). In addition, in order to investigate nonspecific immunological effects, the activity of lysozyme in the serum, spleen, and kidney was measured by concentration, administration method, and time after dissection of olive flounder. As a result, it could be understood that even if the concentration of Mebendazole increases or the administration method is different, it does not affect the activity of lysozyme (Table 5). Accordingly, it was confirmed that the administration of Mebendazole did not cause any problem in the safety of the fish.

Example 6: Field Test of Mebendazole for Exterminating Scuticociliates

The pharmaceutical efficacy was investigated after administering Mebendazole once daily for 5~7 days to the olive flounder which are infected with scuticociliates in three major domestic olive flounder aquaculture area (Jeju, Wando, Pohang).

First, the natural scuticociliates infection rate of each olive flounder farm was investigated, and the efficacy was investigated after administering Mebendazole accordingly.

TABLE 6

Field test condition of Mebendazole for exterminating scuticociliates

| Region | Test Period | Fish size | Numbers for test | Mean water Temperature | Duration of treatment | Rate of Infection (%) |
|---|---|---|---|---|---|---|
| Wando | From April to early June, 2014 | 17 cm | 2,000 | 20.0° C. | 7 days(30 g/ton/day) | 70(22/30) |
| Pohang | From June to late July, 2014 | 18 cm | 2,500 | 21.8° C. | 7 days(30 g/ton/day) | 70(20/30) |
| Jeju | From August to late September, 2014 | 22 cm | 6,000 | 24.8° C. | 5 days(30 g/ton/day) | 50(15/30) |

Mebendazole was administered once daily for 7 days to two fish tanks keeping infected fish which developed scuticociliatosis in a olive flounder farm in Wando. As a result, the infection rate of scuticociliates before administration was shown to be 70%, but no infection of scuticociliates was detected after administration.

Mebendazole was administered once daily for 7 days to two fish tanks keeping test fish which developed scuticociliatosis in a olive flounder farm in Pohang. As a result, the infection rate of scuticociliates before administration was shown to be 70%, but no infection of scuticociliates was detected after administration.

Mebendazole was administered once daily for 5 days to two fish tanks keeping test fish which developed scuticociliatosis in a olive flounder farm in Juju. As a result, the infection rate of scuticociliates before administration was shown to be 50%, but no infection of scuticociliates was detected after administration.

Example 7: Safety Test According to Administration Field Test of Mebendazole As a result of confirming the extermination effect of scuticociliates according to the administration of Mebendazole through Example 6, a safety test according to the administration of Mebendazole was also conducted for the commercialization of Mebendazole. The test methods were the same as the safety test method according to the administration clinical test of Mebendazole of Example 5, and the blood chemistry characteristics of the olive flounder according to the administration of Mebendazole were investigated in Wando (Table 7), Pohang (Table 8) and Jeju (Table 9) farms.

TABLE 7

| Period | TCHO (mg/dl) | GLU (mg/dl) | GOT (U/l) | GPT (U/l) | ALP (U/l) | TP (g/dl) | TG (mg/dl) | BUN (mg/dl) |
|---|---|---|---|---|---|---|---|---|
| Control | 122.7 | 32.0 | 69 | 18.4 | 106 | 4.74 | 162 | 6.38 |
| 1 D* | 122.9 | 10.7 | 61.6 | 6.5 | 141 | 4.48 | 147 | 4.26 |
| 3 D* | 85.2 | 13.3 | 84.7 | 5.4 | 92 | 3.35 | 101 | 5.08 |
| 6 D* | 118.4 | 9.55 | 58.9 | 2.1 | 138 | 4.08 | 299 | 3.65 |

1 D*, 3 D*, 6 D*: 1 Day, 3 Days, 6 Days after Mebendazole treatment(5 to 7 Days)

TABLE 8

| Period | TCHO (mg/dl) | GLU (mg/dl) | GOT (U/l) | GPT (U/l) | ALP (U/l) | TP (g/dl) | TG (mg/dl) | BUN (mg/dl) |
|---|---|---|---|---|---|---|---|---|
| Control | 328.6 | 55.7 | 31.1 | 6.6 | 390 | 5.5 | 958 | 4.4 |
| 1 D* | 265.5 | 33.2 | 28.9 | 5.8 | 262 | 4.3 | 785 | 4.3 |
| 3 D* | 271.5 | 27.7 | 27.6 | 4.7 | 218 | 4.5 | 564 | 4.1 |
| 6 D* | 291.3 | 59.4 | 26.9 | 5.8 | 340 | 5.2 | 389 | 4.0 |

1 D*, 3 D*, 6 D*: 1 Day, 3 Days, 6 Days after Mebendazole treatment(5 to 7 Days)

TABLE 9

| Period | TCHO (mg/dl) | GLU (mg/dl) | GOT (U/l) | GPT (U/l) | ALP (U/l) | TP (g/dl) | TG (mg/dl) | BUN (mg/dl) |
|---|---|---|---|---|---|---|---|---|
| Control | 154.5 | 35 | 104 | 22.4 | 145 | 5.21 | 188.5 | 6.6 |
| 1 D* | 340.7 | 11.2 | 15.7 | 5.2 | 179 | 7.67 | 584.1 | 6.6 |
| 3 D* | 168.5 | 9 | 17.3 | 5.5 | 42 | 4.77 | 176.8 | 7.3 |
| 6 D* | 175.3 | 11.8 | 16.1 | 1.7 | 58 | 3.39 | 163.5 | 6.2 |

1 D*, 3 D*, 6 D*: 1 Day, 3 Days, 6 Days after Mebendazole treatment(5 to 7 Days)

The control group which is fish infected with scuticociliates shows higher GOT and GPT level in liver than GOT and GPT level of normal olive flounder.

However, it was confirmed that after Mebendazole was administered, the liver index was lowered to the normal range. In general, when drugs are taken, the liver index varies by drug toxicity. However, in the group administered with Mebendazole of the field application concentration range, it was confirmed that it does not affect the liver index, but rather helps the liver index of infected fish. Thus, it could be confirmed that Mebendazole has excellent effects of exterminating scuticociliates, and the safety for fish is assured. In particular, Mebendazole has been shown to be effective not only for immersion administration but also for oral administration. Accordingly, Mebendazole may be effectively used as a composition for exterminating scuticociliates.

As discussed above, the specific portions of the contents of the present disclosure have been described in detail.

Therefore, it is apparent to a person having ordinary skill in the pertinent art that such specific technology is merely a preferable embodiment, and the scope of the present disclosure is not limited thereto. Accordingly, the substantial scope of the present disclosure is defined by the appended claims and their equivalents.

The invention claimed is:

1. A method for exterminating scuticociliates in fish, comprising a step of administering a composition comprising Mebendazole to fish.

2. The method of claim 1, wherein the composition is orally administered or immersing administered.

3. The method of claim 2, wherein Mebendazol is orally administered at a concentration of 150~300 ppm.

4. The method of claim 2, wherein Mebendazol is single immersing administered for 2~4 hours at a concentration of 50~300 ppm; or multiple immersing administered for 3-10 days at a concentration of 10~50 ppm by replacing Mebendazol every day.

5. The method of claim 1, wherein the fish is one or more selected from a group consisting of olive flounder, black rockfish, red seabream and sea bass.

* * * * *

UNITED STATES PATENT AND TRADEMARK OFFICE
CERTIFICATE OF CORRECTION

PATENT NO. : 9,956,204 B2  
APPLICATION NO. : 15/620788  
DATED : May 1, 2018  
INVENTOR(S) : Jung Soo Seo Page 1 of 1

It is certified that error appears in the above-identified patent and that said Letters Patent is hereby corrected as shown below:

On the Title Page

Column 2, Line 7 in Other Publications: author "Barry, R. M., et al." should be -- Parry, R. M., et al. --

Signed and Sealed this  
Fifth Day of June, 2018

Andrei Iancu  
*Director of the United States Patent and Trademark Office*